United States Patent [19]

Vogelstein et al.

[11] Patent Number: 5,728,523
[45] Date of Patent: Mar. 17, 1998

[54] POLYMERASE DELTA MUTATIONS IN COLORECTAL TUMORS WITH REPLICATION ERRORS

[75] Inventors: Bert Vogelstein; Kenneth W. Kinzler, both of Baltimore, Md.

[73] Assignee: The Johns Hopkins University, Baltimore, Md.

[21] Appl. No.: 366,577

[22] Filed: Dec. 30, 1994

[51] Int. Cl.⁶ .............................. C12Q 1/68; C12P 19/34; C07H 21/02; C07H 21/04
[52] U.S. Cl. ........................... 435/6; 435/91.2; 536/23.1; 536/24.3; 536/24.33
[58] Field of Search ............... 435/6, 91.2; 536/23.1, 536/24.3–24.33

[56] References Cited

PUBLICATIONS

Yang et al. "Molecular Cloning of the cDNA for the catalytic subunit of human polymerase delta" Nucleic Acids Research 20(4) 735–745, 1992.

Strand et al. "Destabilization of tracts of simple repetitive DNA in yeast y mutations affecting DNA mismatch repair" Nature 365: 274–276, 1993.

Da Costa et al "polymerase delta variants in RER colorectal tumours" Nature Genetics 9: 10–11, 1995.

Yang et al., "Molecular Cloning of the cDNA for the Catalytic Subunit of human DNA Polymerase δ", *Nucleic Acids Research*, 20(4):735–745 (1992).

Chung et al., "Primary Structure of the Catalytic Subunit of Human DNA Polymerase δ and Chromosomal Location of the Gene", *Proc. Natl. Acad. Sci. USA* 88:11197–11201 (1991).

Strand et al., "Destabilization of Tracts of Simple Repetitive DNA in Yeast by Mutations Affecting DNA Mismatch Repair", *Nature* 365:274–276 (1993).

DaCosta et al., "Polymerase Delta Variants in RER Colorectal Tumors", *Nature Genetics* 9(1):10–11 (1995).

*Primary Examiner*—W. Gary Jones
*Assistant Examiner*—Dianne Rees
*Attorney, Agent, or Firm*—Banner & Witcoff, Ltd.

[57] ABSTRACT

The human pol δ gene, responsible for a replication error phenotype in some colorectal tumors, can be used for diagnostic and therapeutic purposes. It can be used to demonstrate the existence of germline or somatic mutations in replication error (RER⁺) tumor cells.

4 Claims, 3 Drawing Sheets

FIG. 1

|  | Codon | N H<br>↑ ↑ |  | Codon |
|---|---|---|---|---|
| Human | 499 | - NGNDQTRRRLAVYCLKDAYLPLRL | - | 522 |
| Calf | 498 | - NGNDQTRRRLAVYCLKDAFLPLRL | - | 521 |
| S. cerevisiæ | 504 | - NGDSETRRRLAVYCLKDAYLPLRL | - | 527 |
| S. pombe | 483 | - NGTADSRRRLAIYCLKDAYLPQRL | - | 506 |

⟵——— Exo III ———⟶

```
587  I  E  P  L  K  G  Y  Y  D  V  P  I  A  T  L  D  F  S  S  L  Y  P  S  I  M  H  A  H  N  L  C  Y  T  T  L  L  R  P  G  T
     GCACAGAAACTGGGCCTGACTGAGGATCAGTTCATCAGACCCCACCGGGACGAGTTTGTGAAGACTCAGTGGGCTGCCCCAGATCCTGGAGAACCTGCTCAGTGCC
627  A  Q  K  L  G  L  T  E  D  Q  F  I  R  T  P  T  G  D  E  F  V  K  T  S  V  R  K  G  L  L  P  Q  I  L  E  N  L  L  S  A
     CGGAAGAGGGCCAAGGCCGAGCTGGCCAAGGAGACAGACCCCCTCCGGCGCCAGGTCCTGGATGGACGGCAGCTGAAGTGAGCGGCTACACTCCGTATACGGCTTCACTGGCGCC
667  R  R  K  A  K  A  E  L  A  K  E  T  D  P  L  R  R  Q  V  L  D  G  R  Q  L  A  L  K  V  S  A  N  S  V  Y  G  F  T  G  A
     CAGGTGGGCAAGTTGCCCTGACTGACAGATCTCAGGAGCCGTCAGATGATCCGATTCCGGTGCCTCGGTGCATGGTGTGCCGGATTCGGCGTATCGTGCAGTCACTTC
707  Q  V  G  K  L  P  C  L  E  I  S  Q  S  V  T  G  F  G  R  Q  M  I  E  K  T  K  Q  L  V  E  S  K  Y  T  V  E  N  G  Y  S
     ACCAGCGGCCAAGCTGACTGACTGCAATGGTGACACTGACTCCGTATGCGGATTCGGCGCTGTCCTCGGTGCCAGTCTCCGGGACGCCTACGGACCATGGACTGC
747  T  S  A  K  V  V  Y  G  D  T  D  S  V  M  C  R  F  G  V  S  S  V  A  E  A  M  A  L  G  E  A  A  D  W  V  S  G  H  F
     CGTCGCCCATCGGCCTGAGTTGACGTCCTCTTCCCATACTGCTATTCAGCAAGAGCCCTACGCGCCGCCTGTTGGCTGCTACGCACAGGAC
787  P  S  P  I  R  L  E  F  E  K  V  Y  F  P  Y  L  L  I  S  K  K  R  Y  A  G  L  L  F  S  S  R  P  D  A  H  D  R  M  D  C
     AAAGGGCCTGACGGCGGTTGAGGCTCGCCAGGGACACTGCGGCCTGTGCAACTGCGCGCTTCTACTCGCGCCGAGACCTGACGCTGGACGTGGACCGCATGGACTGT
827  K  G  L  E  A  V  R  R  D  N  C  P  L  V  A  N  L  V  T  A  S  L  R  R  L  L  I  D  R  D  P  E  G  A  V  A  H  A  Q  D
     GTCATCTGGACCTGCTGCTGTGCAATCGATATCTCCCAGCCTGTCATCACCGAGGAGCTGCGCCGACTGCTAATCGACCGGGACCCGGAGGGCGCTGTGGCTCACGCTCAG
867  V  I  S  D  L  C  N  R  I  D  I  S  Q  L  V  I  T  K  E  L  T  R  A  A  S  D  Y  A  G  K  Q  A  H  V  E  L  A  E  R
     ATGAGGAAGCGGGACCCGGAGTGCGGCCAGTACTACCTGGAGCAGATGCTGCCGGGCTACATGAAGTGTGCCCGGCTCTATGCCATGGCGAAGGGCGGGATCTGGTGTCTACTGCGGG
907  H  R  K  R  D  P  G  S  A  P  S  L  G  D  R  V  P  Y  V  I  I  S  A  A  K  G  V  A  A  Y  H  K  S  E  D  P  L  F  V  L
     GAGCACAGCCTGCCCATTGACACAGCGGCTACCTGGAGCAGCTGCAGGAGCAGGGCCGGCCACTGCCTCAGCGCACAGTCCTCAGCCACCAGGAGCCGGTGT
947  E  H  S  L  P  I  D  T  Q  Y  Y  L  E  Q  Q  L  A  K  P  L  L  R  I  F  E  P  I  L  G  E  G  R  A  E  A  V  L  R  G
     GACCACACCGGCTGCAAGACGGGAGTCCTGACCGGGAAGGTGTAGAGAAGAGCTGCACATTCGGAATGCCATCGGGCATCGGCGCCAGCGCTGCCAGGTGAGCCTGCAC
987  D  H  T  R  C  K  T  V  L  T  G  K  V  G  G  L  L  A  F  A  K  R  R  N  C  C  I  G  C  R  T  V  L  S  H  Q  A  V  C
     GAGTTCTGCCAGCGGGAGTCTGAGCTGTATCAGAAGGAGGTGTCCCATCTTCCACATCGGCGAGAAGAGACGTGCGGAGGAGACCTGGACACAGTGCCAGCGCTGTCTCCATG
1027 E  F  C  Q  P  R  E  S  E  L  Y  Q  K  E  V  S  H  L  N  A  L  E  E  R  F  S  R  L  W  T  Q  C  R  Q  G  S  L  H
     GAGGAAGGTACTCACTGACTCCAGCCGGACTGTATCCCCATTCTTCTACATGCCGAAGAAGGTGCGGAAAGATCTGGAGGACGAATTAATAAAGTTTCTGACTTTTGCTACA60
1067 E  D  V  I  C  T  S  R  D  C  P  I  F  Y  M  R  K  K  V  R  K  D  L  E  D  Q  E  Q  L  R  R  F  G  P  P  G  P  E  A
     TGGTGACCCTGCCAAGCATCCCATGGGGGGGGACCAGGAGAAGTTCTGACTTTTGCTACA60
1107 W  *
```

POLYMERASE DELTA MUTATIONS IN COLORECTAL TUMORS WITH REPLICATION ERRORS

This invention was made with government support under NIH Grant Number CA35494 awarded by the National Institutes of Health. The government has certain rights in this invention.

TECHNICAL FIELD OF THE INVENTION

The invention relates to a gene which causes replication errors in colorectal and other cancers. In addition, it also relates to biochemical tests which can be used to identify drugs for treatment of affected individuals.

BACKGROUND OF THE INVENTION

Widespread, subtle alterations of the cancer cell genome were first detected in a subset of sporadic colorectal tumors using the arbitrarily-primed polymerase chain reaction (Peinado et al., 1992, "Isolation and characterization of allelic losses and gains in colorectal tumors by arbitrarily primed polymerase chain reaction." *Proc. Natl. Acad. Sci. USA* 89, 10065–10069.). These alterations were subsequently found to represent deletions of up to 4 nucleotides in genomic polyA tracts (Ionov et al., 1993, "Ubiquitous somatic mutations in simple repeated sequences reveal a new mechanism for colonic carcinogenesis." *Nature* 363, 558–561). Other studies showed that a similar, distinctive subgroup of sporadic tumors had insertions or deletions in a variety of simple repeated sequences, particularly micsrosatellite sequences consisting of dinucleotide or trinucleotide repeats (Ionov et al., 1993, supra; Thibodeau et al., 1993, "Microsatellite instability in cancer of the proximal colon." *Science* 260, 816–819; Aaltonen et al., 1993, "Clues to the pathogenesis of familial colorectal cancer." *Science* 260, 812–816). Interestingly, these sporadic tumors had certain features in common with those developing in Hereditary Non-Polyposis Colorectal Cancer (HNPCC) kindreds, such as a tendency to be located on the right side of the colon and to be near-diploid. These and other data suggested that HNPCC and a subset of sporadic tumors were associated with a heritable defect causing replication errors (RER) of microsatellites (Ionov et al., 1993, supra; Aaltonen et al., 1993, supra).

The mechanism underlying the postulated defect could not be determined from the study of tumor DNA, but studies in simpler organisms provided an intriguing possibility (Levinson and Gutman, 1987, "High frequencies of short frameshifts in poly-CA/TG tandem repeats borne by bacteriophage M13 in *Escherichia coli* K-12." *Nucleic Acids Research* 15, 5323–5338; Strand et al., 1993, "Destabilization of tracts of simple repetitive DNA in yeast by mutations affecting DNA mismatch repair." *Nature* 365, 274–276). This work showed that bacteria and yeast containing defective mismatch repair genes manifest instability of dinucleotide repeats. The disruption of genes primarily involved in DNA replication or recombination had no apparent effect on the fidelity of microsatellite replication (reviewed in Kunkel, 1993, "Slippery DNA and diseases." *Nature* 365, 207–208). These pivotal studies suggested that defective mismatch repair might be responsible for the microsatellite alterations in the tumors from HNPCC patients (Strand et al., 1993, supra).

The replication error (RER$^+$) phenotype is characterized by genetic instability, particularly in microsatellite sequences. This phenotype occurs in both sporadic and hereditary forms of colorectal cancer. Ionov, Y. M. et al. *Nature* 363, 558–561 (1993). Thibodeau, S. N., Bren, G. & Schaid, D. *Science* 260, 816–819 (1993). Aaltonen, L. A. et al. *Science* 260, 812–816 (1993). In the hereditary form, mutations of mismatch repair genes are usually responsible for the instability. In many sporadic tumors, however, mutations of the four known mismatch repair (MMR) genes are apparently absent.

Thus there is a need in the art to identify other genes and proteins responsible for the replication error phenotype found in both hereditary and sporadic tumors. Identification of the gene and protein would allow more widespread diagnostic screening for hereditary non-polyposis colorectal cancer than is currently possible. Identification of the involved gene and protein would also enable the rational screening of compounds for use in drug therapy of hereditary non-polyposis colorectal cancer, and would enable gene therapy for affected individuals.

SUMMARY OF THE INVENTION

It is an object of the invention to provide DNA molecules which contain specific mutations which cause a replication error phenotype in tumors.

It is another object of the invention to provide methods of treating persons who are predisposed to hereditary non-polyposis colorectal cancer.

It is still another object of the invention to provide methods for determining a predisposition to cancer.

It is a further object of the invention to provide methods for screening test compounds to identify therapeutic agents for treating persons predisposed to hereditary non-polyposis colorectal cancer.

It is still another object of the invention to provide a mutant protein which is involved in faulty human DNA mismatch repair.

It is yet another object of the invention to provide a transgenic animal for studying potential therapies for hereditary non-polyposis colorectal cancer.

It is still another object of the invention to provide a method of treating a person having an RER$^+$ tumor to prevent accumulation of somatic mutations leading to resistance to an anti-cancer therapeutic agent.

These and other objects of the invention are provided by one or more of the embodiments described below. In one embodiment of the invention an isolated and purified DNA molecule is provided. The molecule has a sequence of at least about 20 nucleotides of a pol δ allele found in a tumor wherein said DNA molecule contains a mutation relative to wild-type pol δ shown in SEQ ID NO:1.

In yet another embodiment of the invention a method of treating a person predisposed to hereditary non-polyposis colorectal cancer is provided. The method prevents accumulation of somatic mutations. The method involves administering a DNA molecule which has a sequence of at least about 20 nucleotides of pol δ, as shown in SEQ ID NO:1, to a person having a mutation in a pol δ allele which predisposes the person to hereditary non-polyposis colorectal cancer, wherein said DNA molecule is sufficient to remedy the mutation in a pol δ allele of the person.

In another embodiment of the invention a method is provided for determining a predisposition to cancer. The method involves testing a body sample of a human to ascertain the presence of a mutation in pol δ which affects DNA polymerase delta expression or DNA polymerase delta function, the presence of such a mutation indicating a predisposition to cancer.

In still another embodiment of the invention a method is provided for screening to identify therapeutic agents which can prevent or ameliorate tumors. The screening method involves contacting a test compound with a DNA polymerase delta protein or a cell; determining the ability of the DNA polymerase delta protein or the cell to perform DNA mismatch repair, a test compound which increases the ability of said DNA polymerase delta protein or said cell to perform DNA mismatch repair being a potential therapeutic agent.

In another embodiment of the invention an isolated and purified mutant protein is provided. The protein has the sequence of a DNA polymerase delta found in a tumor.

In still another embodiment of the invention a transgenic animal is provided. The transgenic (nonhuman) animal maintains a pol δ allele in its germline. The pol δ allele is one which is found in humans having hereditary non-polyposis colorectal cancer or in RER+ tumors. Also provided are animals which have no wild-type pol δ alleles, due to mutations introduced.

Thus the present invention provides the art with the sequence of a mutant gene which is involved in the replication error phenotype of tumors and may also be responsible for some cases of hereditary non-polyposis colorectal cancer. This enables the art to practice a variety of techniques to identify persons at risk of developing a variety of cancers and to treat them to prevent such cancers from actually developing or progressing.

BRIEF DESCRIPTION OF THE DRAWINGS

FIG. 1 shows the protein sequence alignment of Exo III and flanking codons of normal human, calf, *S. cerevisiae* and *S. pombe* DNA polymerase delta. Amino acids that differed in the studied tumors are indicated. A 1.1 kb fragment of human pol δ cDNA corresponding to codons 227 to 587 SEQ ID NO:1 was amplified using primers 5'-CCT GGA ACA GGG CAT CCG-3' SEQ ID NO:5 and 5'-CGA TGA CAG TGG CTC CCG-3' SEQ ID NO:6. The nucleotide sequence of codons 499–522 was determined using the primer 5'-TGT CAG CAT GGT GGG CCG-3' SEQ ID NO:7.

Figure 2A:
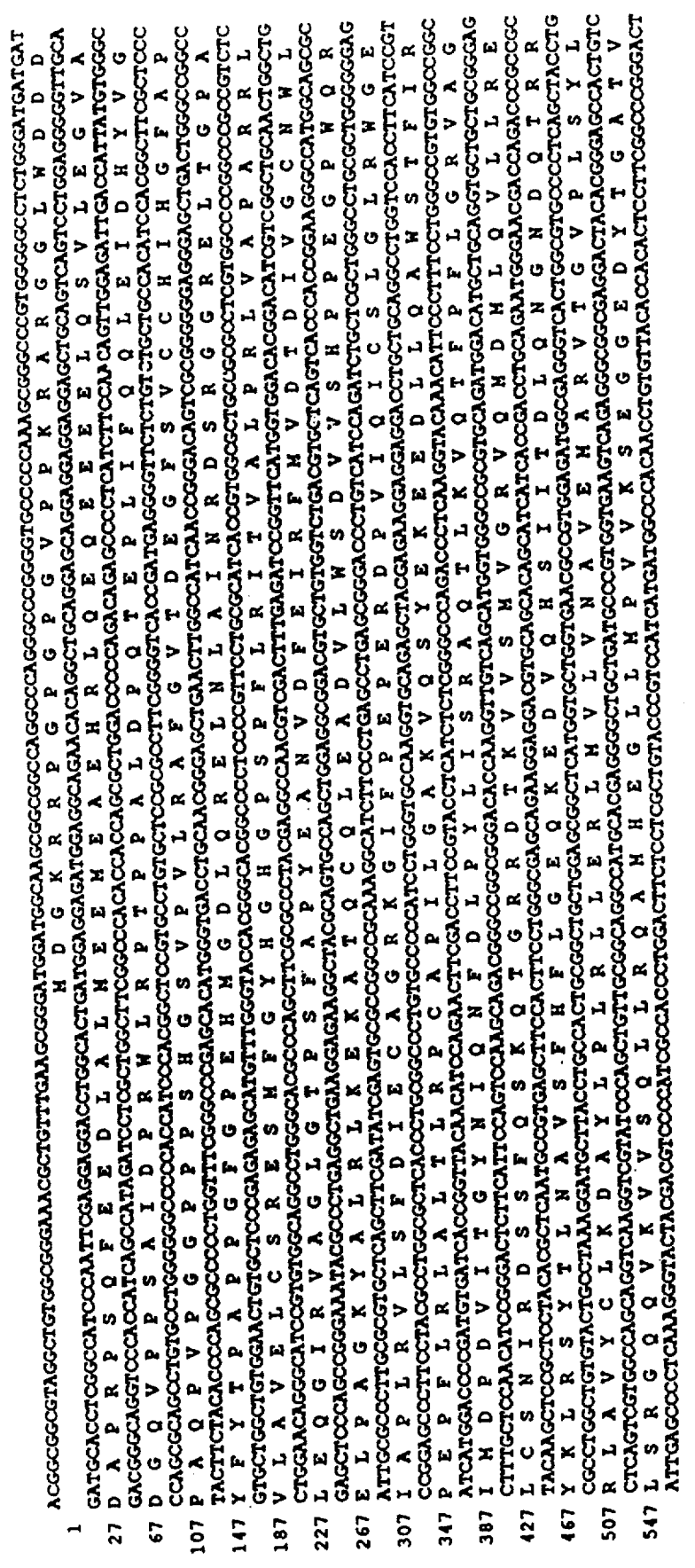

FIG. 2A and 2B show the nucleotide sequence and amino acid sequences of wild type polymerase δ (SEQ ID. NO:1 and SEQ ID NO:2).

DETAILED DESCRIPTION OF THE PREFERRED EMBODIMENTS

It is a discovery of the present invention that mutations in the human gene pol δ are found in human tumors of the RER+ phenotype, which appear not to have mutations in the known mismatch repair genes. The cDNA sequence of wild-type pol δ is shown in SEQ ID NO:1. This gene encodes DNA polymerase delta, which contains a 3'–5' exonuclease activity. It is a further discovery of the present invention that mutation of the pol δ gene causes cells to accumulate other mutations. Thus DNA polymerase delta mutations lead to a mismatch repair defect. The replication error phenotype (RER+) found in both sporadic and hereditary non-polyposis colorectal cancer is characterized by variations (insertions and deletions) in microsatellite DNA.

Useful DNA molecules according to the invention are those which will specifically hybridize to pol δ mutant sequences found in RER+ tumors. Typically these are at least about 20 nucleotides in length and have a mutation relative to the wild-type nucleotide sequence as shown in SEQ ID NO:1. The DNA molecules contain a mutation which has been found in RER+ tumors (HNPCC patients or sporadic tumors). Such molecules can be used as allele-specific oligonucleotide probes to track a particular mutation through a family. Such molecules can be labeled, according to any technique known in the art, such as with radiolabels, fluorescent labels, enzymatic labels, sequence tags, etc.

According to some aspects of the invention, it is desirable that a wild-type cDNA, which encodes all or a part of the DNA polymerase delta protein as shown in SEQ ID NO:2, be used. To obtain expression of the protein the DNA sequence can be operably linked to appropriate control sequences, such as promotor, Kozak consensus, and terminator sequences.

A person who is predisposed to develop cancers due to inheritance of a mutant pol δ allele can be treated by administration of a DNA molecule which contains all or a part of the normal pol δ gene sequence as shown in SEQ ID NO:1. A portion of the gene sequence will be useful when it spans the location of the mutation which is present in the mutant allele, so that a double recombination event between the mutant allele and the normal portion "corrects" the defect present in the person. A portion of the gene can also be usefully administered when it encodes enough of the protein to express a functional 3'–5' exonuclease enzyme. Such a portion need not necessarily recombine with the mutant allele, but can be maintained at a separate locus in the genome or on an independently replicating vector. Means for administering DNA to humans are known in the art, and any can be used as is convenient. A variety of vectors are also known for this purpose. According to some techniques vectors are not required. Such techniques are well known to those of skill in the art.

Also contemplated as part of the present invention is the use of a combined anti-neoplastic therapy regimen. Such a combined regimen is useful for patients having an RER+ tumor, whether sporadic or associated with HNPCC. The regimen combines any standard anti-neoplastic therapy to which a patient can become resistant and pol δ gene therapy, as described above. By remedying the defect present in RER+ cells, i.e., a pol δ mutation, the likelihood of the tumor developing a resistance mutation is greatly diminished. By delaying or preventing the onset of resistance, the lives of cancer patients can be prolonged. In addition, such prevention of resistance allows a greater degree of tumor destruction by the therapeutic agent. Examples of anti-neoplastic therapies which can be combined with pol δ gene therapy are hormones, radiation, cytotoxic drugs, cytotoxins, and antibodies.

Body samples can be tested to determine whether the pol δ gene is normal or mutant. Mutations are those deviations from the sequence shown in SEQ ID NO:1 which are associated with disease and which cause a change in pol δ protein function or expression. Such mutations include, but are not limited to, nonconservative amino acid substitutions, deletions, premature terminations and frameshifts. It is believed that such mutations reside in the domains termed Exo I, Exo II, and Exo III. However, mutations in other sites could affect the exonuclease activity of DNA polymerase delta. Suitable body samples for testing include those comprising DNA, RNA, or protein, obtained from biopsies, blood, prenatal, or embryonic tissues, for example.

Provided with the information that a defect causing HNPCC and/or sporadic RER+ tumors is in an exonuclease which affects DNA mismatch repair, one can perform assays on test compounds and compositions to determine if the compounds will remedy the defect. Such therapeutic compounds could bind to missense DNA polymerase delta mutant proteins to restore the proteins to the normal, active conformation. Alternatively, such therapeutic compounds could stimulate the expression of alternate pathways for mismatch repair. Screening for such therapeutic compounds could be performed by contacting test compounds with cells, either normal cells or those with a pol δ mutation found in a tumor. The mismatch repair ability of the cells which were contacted with the test compounds is compared with the ability of the same cells which were not contacted with the test compounds. Such activity can be tested as is known in the art. See, for example, Levinson and Gutman, 1987, and Strand et al., 1993. Observation of changes in microsatellite DNA in cells is one way of assessing mismatch repair activity. Another approach is to assay DNA mismatch repair in vitro in nuclear extracts. See Holmes, 1990; Thomas, 1991; and Fang, 1993. Exonuclease activity can also be assayed.

Provided with the cDNA sequence of pol δ and the amino acid sequence of the protein, one of ordinary skill in the art can readily produce DNA polymerase delta protein, isolated and purified from other human proteins. For example, recombinant cells or organisms can be used to produce the protein in bacteria, yeast, or other convenient cell system. The isolated and purified protein can be used in screening for new therapeutic agents, for example, in in vitro assays of DNA mismatch repair. The protein can also be used to raise antibodies against pol δ. Therapeutic administration of the protein is also contemplated.

Transgenic animals are also contemplated by the present invention. These animals have pol δ alleles which are associated with HNPCC or sporadic tumors inserted in their germline. Such animals provide model systems for testing drugs and other therapeutic agents to prevent or retard the development of tumors. Also contemplated are genetically engineered animals which contain one or more mutations in their own pol δ genes. The mutations will be engineered to correspond to mutations found in pol δ alleles which are found in HNPCC-affected individuals or in other human RER$^+$ tumors. Animals with both native pol δ alleles inactivated and containing a human wild-type or mutant pol δ allele are particularly desirable.

EXAMPLES

Mutator phenotypes have been extensively studied in unicellular organisms such as E. coli and S. cerevisiae. In both of these organisms, mutations in the 3'-5' exonuclease "proofreading" domain of DNA polymerases can cause a mutator phenotype with similarities to that observed in RER$^+$ cancers. Particularly intriguing was the observation that mutations affecting the exonuclease activity associated with E. coli pol III or S. cerevisiae pol δ can cause a mismatch repair deficiency or microsatellite instability. Schaaper, R-M. & Padman, M. *EMBO J* 8, 3511–3516 (1989); Strand, M., et al. *Nature* 365, 274–276 (1993). These observations prompted us to study the exonuclease domain of human pol δ

Eight colorectal cancer cell lines which displayed microsatellite instability (Shibata, D. et al. *Nature Genet.* 6, 273–281 (1994)) and were negative in screens for mutations of the four known human genes were studied. All cell lines (HCT15, DLD-1, LS180, RKO, 587X, VACO 444, VACO 457, and VACO 481) were examined for gene mutations by reverse transcriptase- polymerase chain reaction (RT-PCR) analysis to detect abnormal transcripts and by the in vitro synthesized protein assay to detect abnormal polypeptides. These assays detect over 90% of the mutations previously identified in the human mismatch repair (MMR) genes. Liu, B. et al. *Cancer Research* 54, 4590–4594 (1994). Additionally, the sequences of the entire coding regions of the MMR genes in 587X, VACO 444, VACO 457, and VACO 481 were determined. No gene abnormalities were detected by any of these assays in any of the cell lines. RNA from these lines was used to amplify a 1.1 kb fragment of pol δ cDNA (see description of FIG. 1). This fragment contains the three highly conserved regions, termed Exo I, Exo II, and Exo III, thought to be involved in 3'-5' exonuclease activity. Chung, D. W. et al. *Proc. Natl. Acad. Sci. USA* 88, 11197–11201 (1991); Yang, C.-L. et al. *Nucleic Acids Res.* 20, 735–745 (1992). The sequence of the RT-PCR products revealed variants in three of the lines, each of which was confirmed in separate RT-PCR and sequencing reactions. The variant in the tumor from 587X resulted in an Asp to Asn substitution at codon 502 due to a G to A transition. Codon 502 is just proximal to the Exo III domain (FIG. 1). This variant was also found in the normal colon of patient 587X. A second variant was found in both cell lines DLD-1 and HCT15, resulting in an Arg to His substitution at codon 506 due to a G to A transition at a CpG site. Codon 506 is within the Exo III domain at a position conserved throughout evolution (FIG. 1). The DLD-1 and HCT15 lines probably originated from the same patient, as they were derived from the same laboratory, have identical mutations in RAS and p53 (Shibata, D. et al. *Nature Genet.* 6, 273–281 (1994)), have identical alleles detected by four minisatellite markers (unpublished data), and have the same pol δ sequence at codon 506. Fresh cultures of DLD-1 and HCT15 were obtained from the American Type Culture Collection, and the same pol δ variant was found. Normal tissue from the patient giving rise to these cell lines was not available. Neither of the variants at codons 502 or 506, nor any other variations between codons 499 and 522, were found in 100 control chromosomes.

Though the variants detected are not common polymorphisms, they should be interpreted cautiously. The codon 502 variant was found in the normal colon of patent 587X, who had no family history of neoplasia and did not develop cancer until the age of 70. The codon 506 mutation in DLD-1/HCT15 could have been somatic. However, none of eight RER$^+$ tumors from patents with germline mismatch repair gene mutations had a variation in the Exo III region of pol δ, and clonal mutations in nonmicrosatellite sequences are uncommon even in RER$^+$ tumors.

There was a remarkable similarity between the hypermutability in DLD-1/HCT15 and that in *S. cerevisiae* strains harboring mutations in the exonuclease domain of pol δ. DLD-1/HCT15 has a relatively low rate of microsatellite instability compared to tumor cell lines with mutations of hMSH2 or hMLHI, but an equivalently elevated rate of mutation at the HPRT locus. Shibata, supra; Bhattacharyya, N. P. et al. *Proc. Natl. Acad. Sci. USA* 91, 6319–6323 (1994). Analogously, *S. cerevisiae* pol δ exonuelease mutants have a relatively low level of microsatellite instability compared to yMSH2 and yMLH1 mutants (Strand, supra) but a high rate of chromosomal mutability. Simon, M., et al., *EMBO J.* 10, 2165–2170 (1991). Indeed, exonuclease deficient mutants or E. coli and S. cerevisiae, including Exo III region mutants, are among the most potent mutators known. Schaaper, supra, Strand, supra, Bhattacharyya, supra, Simon, supra, and Foury, F. & Vanderstraeten, S. *EMBO J.* 11, 2717–2726 (1992). The HPRT mutational spectrum in DLD-1/HCT15 is also different than that in lines with a MMR gene mutation, analogous to the difference between the mutational spectra of yeast strains with pol δ and MMR gene mutations. Strand, supra.

It has also been shown that extracts of DLD-1/HCT15 have a deficiency in mismatch repair in vitro. Umar, A. et al. *J. Biol. Chem.* 269, 14367-14370 (1994). How could a mutation in the exonuclease domain of a polymerase result in such a deficiency? It has been suggested that a proofreading defect could lead to numerous mispairs, resulting in saturation of the mismatch repair apparatus. Schaaper, supra. Indeed, an exonuclease mutant of *E. coli* has been shown to result in a profound mismatch repair deficiency during active growth that can be corrected by overexpression of mismatch repair genes. Schaaper, supra.

---

We claim:

1. A method of determining a predisposition to colorectal cancer comprising:

testing a body sample of a human to ascertain the presence of a mutation in pol δ which affects DNA polymerase delta expression or DNA polymerase delta function, the presence of such a mutation indicating a predisposition to colorectal cancer.

2. The method of claim 1 wherein the sample is DNA.

3. The method of claim 1 wherein the sample is RNA.

4. The method of claim 1 wherein the sample is isolated from prenatal or embryonic cells.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 3435 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: CDS
        ( B ) LOCATION: 43..3364

( x i ) SEQUENCE DESCRIPTION: SEQ ID NO:1:

```
ACGGCGGCGT AGGCTGTGGC GGGAAACGCT GTTTGAAGCG GG ATG GAT GGC AAG          54
                                                Met Asp Gly Lys
                                                 1

CGG CGG CCA GGC CCA GGG CCC GGG GTG CCC CCA AAG CGG GCC CGT GGG        102
Arg Arg Pro Gly Pro Gly Pro Gly Val Pro Pro Lys Arg Ala Arg Gly
 5               10                  15                  20

GGC CTC TGG GAT GAT GAT GAT GCA CCT TGG CCA TCC CAA TTC GAG GAG        150
Gly Leu Trp Asp Asp Asp Asp Ala Pro Trp Pro Ser Gln Phe Glu Glu
                 25                  30                  35

GAC CTG GCA CTG ATG GAG GAG ATG GAG GCA GAA CAC AGG CTG CAG GAG        198
Asp Leu Ala Leu Met Glu Glu Met Glu Ala Glu His Arg Leu Gln Glu
         40                  45                  50

CAG GAG GAG GAG GAG CTG CAG TCA GTC CTG GAG GGG GTT GCA GAC GGG        246
Gln Glu Glu Glu Glu Leu Gln Ser Val Leu Glu Gly Val Ala Asp Gly
             55                  60                  65

CAG GTC CCA CCA TCA GCC ATA GAT CCT CGC TGG CTT CGG CCC ACA CCA        294
Gln Val Pro Pro Ser Ala Ile Asp Pro Arg Trp Leu Arg Pro Thr Pro
 70                  75                  80

CCA GCG CTG GAC CCC CAG ACA GAG CCC CTC ATC TTC CAA CAG TTG GAG        342
Pro Ala Leu Asp Pro Gln Thr Glu Pro Leu Ile Phe Gln Gln Leu Glu
 85                  90                  95                 100

ATT GAC CAT TAT GTG GGC CCA GCG CAG CCT GTG CCT GGG GGG CCC CCA        390
Ile Asp His Tyr Val Gly Pro Ala Gln Pro Val Pro Gly Gly Pro Pro
                105                 110                 115

CCA TCC CGC GGC TCC GTG CCT GTG CTC CGC GCC TTC GGG GTC ACC GAT        438
Pro Ser Arg Gly Ser Val Pro Val Leu Arg Ala Phe Gly Val Thr Asp
                120                 125                 130

GAG GGG TTC TCT GTC TGC TGC CAC ATC CAC GGC TTC GCT CCC TAC TTC        486
Glu Gly Phe Ser Val Cys Cys His Ile His Gly Phe Ala Pro Tyr Phe
                135                 140                 145
```

-continued

| | | | | | | | | | | | | | | | | |
|---|---|---|---|---|---|---|---|---|---|---|---|---|---|---|---|---|
| TAC | ACC | CCA | GCG | CCC | CCT | GGT | TTC | GGG | CCC | GAG | CAC | ATG | GGT | GAC | CTG | 534 |
| Tyr | Thr | Pro | Ala | Pro | Pro | Gly | Phe | Gly | Pro | Glu | His | Met | Gly | Asp | Leu | |
| | 150 | | | | 155 | | | | | 160 | | | | | | |
| CAA | CGG | GAG | CTG | AAC | TTG | GCC | ATC | AGC | CGG | GAC | AGT | CGC | GGG | GGG | AGG | 582 |
| Gln | Arg | Glu | Leu | Asn | Leu | Ala | Ile | Ser | Arg | Asp | Ser | Arg | Gly | Gly | Arg | |
| 165 | | | | 170 | | | | | 175 | | | | | 180 | | |
| GAG | CTG | ACT | GGG | CCG | GCC | GTG | CTG | GCT | GTG | GAA | CTG | TGC | TCC | CGA | GAG | 630 |
| Glu | Leu | Thr | Gly | Pro | Ala | Val | Leu | Ala | Val | Glu | Leu | Cys | Ser | Arg | Glu | |
| | | | | 185 | | | | 190 | | | | | 195 | | | |
| AGC | ATG | TTT | GGG | TAC | CAC | GGG | CAC | GGC | CCC | TCC | CCG | TTC | CTG | CGC | ATC | 678 |
| Ser | Met | Phe | Gly | Tyr | His | Gly | His | Gly | Pro | Ser | Pro | Phe | Leu | Arg | Ile | |
| | | | 200 | | | | 205 | | | | | 210 | | | | |
| ACC | GTG | GCG | CTG | CCG | CGC | CTC | GTG | GCC | CCG | GCC | CGC | CGT | CTC | CTG | GAA | 726 |
| Thr | Val | Ala | Leu | Pro | Arg | Leu | Val | Ala | Pro | Ala | Arg | Arg | Leu | Leu | Glu | |
| | | 215 | | | | 220 | | | | | 225 | | | | | |
| CAG | GGC | ATC | CGT | GTG | GCA | GGC | CTG | GGC | ACG | CCC | AGC | TTC | GCG | CCC | TAC | 774 |
| Gln | Gly | Ile | Arg | Val | Ala | Gly | Leu | Gly | Thr | Pro | Ser | Phe | Ala | Pro | Tyr | |
| | 230 | | | | 235 | | | | | 240 | | | | | | |
| GAG | GCC | AAC | GTC | GAC | TTT | GAG | ATC | CGG | TTC | ATG | GTG | GAC | ACG | GAC | ATC | 822 |
| Glu | Ala | Asn | Val | Asp | Phe | Glu | Ile | Arg | Phe | Met | Val | Asp | Thr | Asp | Ile | |
| 245 | | | | 250 | | | | | 255 | | | | | 260 | | |
| GTC | GGC | TGC | AAC | TGG | CTG | GAG | CTC | CCA | GCT | GGG | AAA | TAC | GCC | CTG | AGG | 870 |
| Val | Gly | Cys | Asn | Trp | Leu | Glu | Leu | Pro | Ala | Gly | Lys | Tyr | Ala | Leu | Arg | |
| | | | | 265 | | | | | 270 | | | | | 275 | | |
| CTG | AAG | GAG | AAG | GCT | ACG | CAG | TGC | CAG | CTG | GAG | GCG | GAC | GTG | CTG | TGG | 918 |
| Leu | Lys | Glu | Lys | Ala | Thr | Gln | Cys | Gln | Leu | Glu | Ala | Asp | Val | Leu | Trp | |
| | | | 280 | | | | | 285 | | | | | 290 | | | |
| TCT | GAC | GTG | GTC | AGT | CAC | CCA | CCG | GAA | GGG | CCA | TGG | CAG | CGC | ATT | GCG | 966 |
| Ser | Asp | Val | Val | Ser | His | Pro | Pro | Glu | Gly | Pro | Trp | Gln | Arg | Ile | Ala | |
| | | 295 | | | | 300 | | | | | 305 | | | | | |
| CCC | TTG | CGC | GTG | CTC | AGC | TTC | GAT | ATC | GAG | TGC | GCC | GGC | CGC | AAA | GGC | 1014 |
| Pro | Leu | Arg | Val | Leu | Ser | Phe | Asp | Ile | Glu | Cys | Ala | Gly | Arg | Lys | Gly | |
| | 310 | | | | 315 | | | | | 320 | | | | | | |
| ATC | TTC | CCT | GAG | CCT | GAG | CGG | GAC | CCT | GTC | ATC | CAG | ATC | TGC | TCG | CTG | 1062 |
| Ile | Phe | Pro | Glu | Pro | Glu | Arg | Asp | Pro | Val | Ile | Gln | Ile | Cys | Ser | Leu | |
| 325 | | | | 330 | | | | | 335 | | | | | 340 | | |
| GGC | CTG | CGC | TGG | GGG | GAG | CCG | GAG | CCC | TTC | CTA | CGC | CTG | GCG | CTC | ACC | 1110 |
| Gly | Leu | Arg | Trp | Gly | Glu | Pro | Glu | Pro | Phe | Leu | Arg | Leu | Ala | Leu | Thr | |
| | | | | 345 | | | | | 350 | | | | | 355 | | |
| CTG | CGG | CCC | TGT | GCC | CCC | ATC | CTG | GGT | GCC | AAG | GTG | CAG | AGC | TAC | GAG | 1158 |
| Leu | Arg | Pro | Cys | Ala | Pro | Ile | Leu | Gly | Ala | Lys | Val | Gln | Ser | Tyr | Glu | |
| | | | 360 | | | | 365 | | | | | 370 | | | | |
| AAG | GAG | GAG | GAC | CTG | CTG | CAG | GCC | TGG | TCC | ACC | TTC | ATC | CGT | ATC | ATG | 1206 |
| Lys | Glu | Glu | Asp | Leu | Leu | Gln | Ala | Trp | Ser | Thr | Phe | Ile | Arg | Ile | Met | |
| | | 375 | | | | 380 | | | | | 385 | | | | | |
| GAC | CCC | GAC | GTG | ATC | ACC | GGT | TAC | AAC | ATC | CAG | AAC | TTC | GAC | CTT | CCG | 1254 |
| Asp | Pro | Asp | Val | Ile | Thr | Gly | Tyr | Asn | Ile | Gln | Asn | Phe | Asp | Leu | Pro | |
| | 390 | | | | 395 | | | | | 400 | | | | | | |
| TAC | CTC | ATC | TCT | CGG | GCC | CAG | ACC | CTC | AAG | GTA | CAA | ACA | TTC | CCT | TTC | 1302 |
| Tyr | Leu | Ile | Ser | Arg | Ala | Gln | Thr | Leu | Lys | Val | Gln | Thr | Phe | Pro | Phe | |
| 405 | | | | 410 | | | | | 415 | | | | | 420 | | |
| CTG | GGC | CGT | GTG | GCC | GGC | CTT | TGC | TCC | AAC | ATC | CGG | GAC | TCT | TCA | TTC | 1350 |
| Leu | Gly | Arg | Val | Ala | Gly | Leu | Cys | Ser | Asn | Ile | Arg | Asp | Ser | Ser | Phe | |
| | | | | 425 | | | | | 430 | | | | | 435 | | |
| CAG | TCC | AAG | CAG | ACG | GGC | CGG | CGG | GAC | ACC | AAG | GTT | GTC | AGC | ATG | GTG | 1398 |
| Gln | Ser | Lys | Gln | Thr | Gly | Arg | Arg | Asp | Thr | Lys | Val | Val | Ser | Met | Val | |
| | | | 440 | | | | 445 | | | | | 450 | | | | |
| GGC | CGC | GTG | CAG | ATG | GAC | ATG | CTG | CAG | GTG | CTG | CTG | CGG | GAG | TAC | AAG | 1446 |
| Gly | Arg | Val | Gln | Met | Asp | Met | Leu | Gln | Val | Leu | Leu | Arg | Glu | Tyr | Lys | |
| | | 455 | | | | 460 | | | | | 465 | | | | | |

| | | | | | | | | | | | | | | | | |
|---|---|---|---|---|---|---|---|---|---|---|---|---|---|---|---|---|
| CTC | CGC | TCC | CAC | ACG | CTC | AAT | GCC | GTG | AGC | TTC | CAC | TTC | CTG | GGC | GAG | 1494 |
| Leu | Arg | Ser | His | Thr | Leu | Asn | Ala | Val | Ser | Phe | His | Phe | Leu | Gly | Glu | |
| | 470 | | | | 475 | | | | | 480 | | | | | | |
| CAG | AAG | GAG | GAC | GTG | CAG | CAC | AGC | ATC | ATC | ACC | GAC | CTG | CAG | AAT | GGG | 1542 |
| Gln | Lys | Glu | Asp | Val | Gln | His | Ser | Ile | Ile | Thr | Asp | Leu | Gln | Asn | Gly | |
| 485 | | | | | 490 | | | | | 495 | | | | | 500 | |
| AAC | GAC | CAG | ACC | CGC | CGC | CGC | CTG | GCT | GTG | TAC | TGC | CTG | AAG | GAT | GCC | 1590 |
| Asn | Asp | Gln | Thr | Arg | Arg | Arg | Leu | Ala | Val | Tyr | Cys | Leu | Lys | Asp | Ala | |
| | | | | 505 | | | | | 510 | | | | | 515 | | |
| TAC | CTG | CCA | CTG | CGG | CTG | CTG | GAG | CGG | CTC | ATG | GTG | CTG | GTG | AAC | GCC | 1638 |
| Tyr | Leu | Pro | Leu | Arg | Leu | Leu | Glu | Arg | Leu | Met | Val | Leu | Val | Asn | Ala | |
| | | | 520 | | | | | 525 | | | | | 530 | | | |
| GTG | GAG | ATG | GCG | AGG | GTC | ACT | GGC | GTG | CCC | CTC | AGC | TAC | CTG | CTC | AGT | 1686 |
| Val | Glu | Met | Ala | Arg | Val | Thr | Gly | Val | Pro | Leu | Ser | Tyr | Leu | Leu | Ser | |
| | | 535 | | | | | 540 | | | | | 545 | | | | |
| CGT | GGC | CAG | CAG | GTC | AAA | GTC | GTA | TCC | CAG | CTG | TTG | CGG | CAG | GCC | ATG | 1734 |
| Arg | Gly | Gln | Gln | Val | Lys | Val | Val | Ser | Gln | Leu | Leu | Arg | Gln | Ala | Met | |
| 550 | | | | | 555 | | | | | 560 | | | | | | |
| CAC | GAG | GGG | CTG | CTG | ATG | CCC | GTG | GTG | AAG | TCA | GAG | GGC | GGC | GAG | GAC | 1782 |
| His | Glu | Gly | Leu | Leu | Met | Pro | Val | Val | Lys | Ser | Glu | Gly | Gly | Glu | Asp | |
| 565 | | | | | 570 | | | | | 575 | | | | | 580 | |
| TAC | ACG | GGA | GCC | ACT | GTC | ATC | GAG | CCC | CTC | AAA | GGG | TAC | TAC | GAC | GTC | 1830 |
| Tyr | Thr | Gly | Ala | Thr | Val | Ile | Glu | Pro | Leu | Lys | Gly | Tyr | Tyr | Asp | Val | |
| | | | | 585 | | | | | 590 | | | | | 595 | | |
| CCC | ATC | GCC | ACC | CTG | GAC | TTC | TCC | TCG | CTG | TAC | CCG | TCC | ATC | ATG | ATG | 1878 |
| Pro | Ile | Ala | Thr | Leu | Asp | Phe | Ser | Ser | Leu | Tyr | Pro | Ser | Ile | Met | Met | |
| | | | 600 | | | | | 605 | | | | | 610 | | | |
| GCC | CAC | AAC | CTG | TGT | TAC | ACC | ACG | CTC | CTT | CGG | CCC | GGG | ACT | GCA | CAG | 1926 |
| Ala | His | Asn | Leu | Cys | Tyr | Thr | Thr | Leu | Leu | Arg | Pro | Gly | Thr | Ala | Gln | |
| | | 615 | | | | | 620 | | | | | 625 | | | | |
| AAA | CTG | GGC | CTG | ACT | GAG | GAT | CAG | TTC | ATC | AGG | ACC | CCC | ACC | GGG | GAC | 1974 |
| Lys | Leu | Gly | Leu | Thr | Glu | Asp | Gln | Phe | Ile | Arg | Thr | Pro | Thr | Gly | Asp | |
| | 630 | | | | | 635 | | | | | 640 | | | | | |
| GAG | TTT | GTG | AAG | ACC | TCA | GTG | CGG | AAG | GGG | CTG | CTG | CCC | CAG | ATC | CTG | 2022 |
| Glu | Phe | Val | Lys | Thr | Ser | Val | Arg | Lys | Gly | Leu | Leu | Pro | Gln | Ile | Leu | |
| 645 | | | | | 650 | | | | | 655 | | | | | 660 | |
| GAG | AAC | CTG | CTC | AGT | GCC | CGG | AAG | AGG | GCC | AAG | GCC | GAG | CTG | GCC | AAG | 2070 |
| Glu | Asn | Leu | Leu | Ser | Ala | Arg | Lys | Arg | Ala | Lys | Ala | Glu | Leu | Ala | Lys | |
| | | | | 665 | | | | | 670 | | | | | 675 | | |
| GAG | ACA | GAC | CCC | CTC | CGG | CGC | CAG | GTC | CTG | GAT | GGA | CGG | CAG | CTG | GCG | 2118 |
| Glu | Thr | Asp | Pro | Leu | Arg | Arg | Gln | Val | Leu | Asp | Gly | Arg | Gln | Leu | Ala | |
| | | | 680 | | | | | 685 | | | | | 690 | | | |
| CTG | AAG | GTG | AGC | GCC | AAC | TCC | GTA | TAC | GGC | TTC | ACT | GGC | GCC | CAG | GTG | 2166 |
| Leu | Lys | Val | Ser | Ala | Asn | Ser | Val | Tyr | Gly | Phe | Thr | Gly | Ala | Gln | Val | |
| | | 695 | | | | | 700 | | | | | 705 | | | | |
| GGC | AAG | TTG | CCG | TGC | CTG | GAG | ATC | TCA | CAG | AGC | GTC | ACG | GGG | TTC | GGA | 2214 |
| Gly | Lys | Leu | Pro | Cys | Leu | Glu | Ile | Ser | Gln | Ser | Val | Thr | Gly | Phe | Gly | |
| | 710 | | | | | 715 | | | | | 720 | | | | | |
| CGT | CAG | ATG | ATC | GAG | AAA | ACC | AAG | CAG | CTG | GTG | GAG | TCT | AAG | TAC | ACA | 2262 |
| Arg | Gln | Met | Ile | Glu | Lys | Thr | Lys | Gln | Leu | Val | Glu | Ser | Lys | Tyr | Thr | |
| 725 | | | | | 730 | | | | | 735 | | | | | 740 | |
| GTG | GAG | AAT | GGC | TAC | AGC | ACC | AGT | GCC | AAG | GTG | GTG | TAT | GGT | GAC | ACT | 2310 |
| Val | Glu | Asn | Gly | Tyr | Ser | Thr | Ser | Ala | Lys | Val | Val | Tyr | Gly | Asp | Thr | |
| | | | | 745 | | | | | 750 | | | | | 755 | | |
| GAC | TCC | GTC | ATG | TGC | CGA | TTC | GGC | GTG | TCC | TCG | GTG | GCT | GAG | GCG | ATG | 2358 |
| Asp | Ser | Val | Met | Cys | Arg | Phe | Gly | Val | Ser | Ser | Val | Ala | Glu | Ala | Met | |
| | | | 760 | | | | | 765 | | | | | 770 | | | |
| GCC | CTG | GGG | CGG | GAG | GCC | GCG | GAC | TGG | GTG | TCA | GGT | CAC | TTC | CCG | TCG | 2406 |
| Ala | Leu | Gly | Arg | Glu | Ala | Ala | Asp | Trp | Val | Ser | Gly | His | Phe | Pro | Ser | |
| | | 775 | | | | | 780 | | | | | 785 | | | | |

-continued

```
CCC ATC CGG CTG GAG TTT GAG AAG GTC TAC TTC CCA TAC CTG CTT ATC                                                    2454
Pro Ile Arg Leu Glu Phe Glu Lys Val Tyr Phe Pro Tyr Leu Leu Ile
    790             795                 800

AGC AAG AAG CGC TAC GCG GGC CTC CTC TTC TCC TCC CGG CCC GAC GCC                                                    2502
Ser Lys Lys Arg Tyr Ala Gly Leu Leu Phe Ser Ser Arg Pro Asp Ala
805             810                 815                 820

CAC GAC CGC ATG GAC TGC AAG GGC CTG GAG GCC GTG CGC AGG GAC AAC                                                    2550
His Asp Arg Met Asp Cys Lys Gly Leu Glu Ala Val Arg Arg Asp Asn
                825                 830                 835

TGC CCC CTC GTG GCC AAC CTG GTC ACT GCC TCA CTG CGC CGC CTG CTC                                                    2598
Cys Pro Leu Val Ala Asn Leu Val Thr Ala Ser Leu Arg Arg Leu Leu
            840                 845                 850

ATC GAC CGA GAC CCT GAG GGC GCG GTG GCT CAC GCA CAG GAC GTC ATC                                                    2646
Ile Asp Arg Asp Pro Glu Gly Ala Val Ala His Ala Gln Asp Val Ile
        855                 860                 865

TCG GAC CTG CTG TGC AAC CGC ATC GAT ATC TCC CAG CTG GTC ATC ACC                                                    2694
Ser Asp Leu Leu Cys Asn Arg Ile Asp Ile Ser Gln Leu Val Ile Thr
    870                 875                 880

AAG GAG CTG ACC CGC GCG GCC TCC GAC TAT GCC GGC AAG CAG GCC CAC                                                    2742
Lys Glu Leu Thr Arg Ala Ala Ser Asp Tyr Ala Gly Lys Gln Ala His
885             890                 895                 900

GTG GAG CTG GCC GAG AGG ATG AGG AAG CGG GAC CCC GGG AGT GCG CCC                                                    2790
Val Glu Leu Ala Glu Arg Met Arg Lys Arg Asp Pro Gly Ser Ala Pro
                905                 910                 915

AGC CTG GGC GAC CGC GTC CCC TAC GTG ATC ATC AGT GCC GCC AAG GGT                                                    2838
Ser Leu Gly Asp Arg Val Pro Tyr Val Ile Ile Ser Ala Ala Lys Gly
            920                 925                 930

GTG GCC GCC TAC ATG AAG TCG GAG GAC CCG CTG TTC GTG CTG GAG CAC                                                    2886
Val Ala Ala Tyr Met Lys Ser Glu Asp Pro Leu Phe Val Leu Glu His
        935                 940                 945

AGC CTG CCC ATT GAC ACG CAG TAC TAC CTG GAG CAG CAG CTG GCC AAG                                                    2934
Ser Leu Pro Ile Asp Thr Gln Tyr Tyr Leu Glu Gln Gln Leu Ala Lys
    950                 955                 960

CCC CTC CTG CGC ATC TTC GAG CCC ATC CTG GGC GAG GGC CGT GCC GAG                                                    2982
Pro Leu Leu Arg Ile Phe Glu Pro Ile Leu Gly Glu Gly Arg Ala Glu
965             970                 975                 980

GCT GTG CTA CTG CGG GGG GAC CAC ACG CGC TGC AAG ACG GTG CTC ACG                                                    3030
Ala Val Leu Leu Arg Gly Asp His Thr Arg Cys Lys Thr Val Leu Thr
                985                 990                 995

GGC AAG GTG GGC GGC CTC CTG GCC TTC GCC AAA CGC CGC AAC TGC TGC                                                    3078
Gly Lys Val Gly Gly Leu Leu Ala Phe Ala Lys Arg Arg Asn Cys Cys
            1000                1005                1010

ATT GGC TGC CGC ACA GTG CTC AGC CAC CAG GGA GCC GTG TGT GAG TTC                                                    3126
Ile Gly Cys Arg Thr Val Leu Ser His Gln Gly Ala Val Cys Glu Phe
        1015                1020                1025

TGC CAG CCC CGG GAG TCT GAG CTG TAT CAG AAG GAG GTA TCC CAT CTG                                                    3174
Cys Gln Pro Arg Glu Ser Glu Leu Tyr Gln Lys Glu Val Ser His Leu
    1030                1035                1040

AAT GCC CTG GAG GAG CGC TTC TCG CGC CTC TGG ACG CAG TGC CAG CGC                                                    3222
Asn Ala Leu Glu Glu Arg Phe Ser Arg Leu Trp Thr Gln Cys Gln Arg
1045                1050                1055                1060

TGC CAG GGC AGC CTG CAC GAG GAC GTC ATC TGC ACC AGC CGG GAC TGC                                                    3270
Cys Gln Gly Ser Leu His Glu Asp Val Ile Cys Thr Ser Arg Asp Cys
                1065                1070                1075

CCC ATC TTC TAC ATG CGC AAG AAG GTG CGG AAG GAC CTG GAA GAC CAG                                                    3318
Pro Ile Phe Tyr Met Arg Lys Lys Val Arg Lys Asp Leu Glu Asp Gln
            1080                1085                1090

GAG CAG CTC CTG CGG CGC TTC GGA CCC CCT GGA CCT GAG GCC TGG T                                                      3364
Glu Gln Leu Leu Arg Arg Phe Gly Pro Pro Gly Pro Glu Ala Trp
        1095                1100                1105
```

```
GACCTTGCAA GCATCCCATG GGGCGGGGGC GGGACCAGGG AGAATTAATA AAGTTCTGGA    3424

CTTTTGCTAC A                                                        3435
```

( 2 ) INFORMATION FOR SEQ ID NO:2:

( i ) SEQUENCE CHARACTERISTICS:
        ( A ) LENGTH: 1107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asp  Gly  Lys  Arg  Arg  Pro  Gly  Pro  Gly  Pro  Gly  Val  Pro  Pro  Lys
 1              5                        10                       15

Arg  Ala  Arg  Gly  Gly  Leu  Trp  Asp  Asp  Asp  Ala  Pro  Trp  Pro  Ser
           20                       25                  30

Gln  Phe  Glu  Glu  Asp  Leu  Ala  Leu  Met  Glu  Glu  Met  Glu  Ala  Glu  His
           35                       40                       45

Arg  Leu  Gln  Glu  Gln  Glu  Glu  Glu  Leu  Gln  Ser  Val  Leu  Glu  Gly
      50                       55                       60

Val  Ala  Asp  Gly  Gln  Val  Pro  Ser  Ala  Ile  Asp  Pro  Arg  Trp  Leu
 65                       70                  75                       80

Arg  Pro  Thr  Pro  Pro  Ala  Leu  Asp  Pro  Gln  Thr  Glu  Pro  Leu  Ile  Phe
                     85                       90                       95

Gln  Gln  Leu  Glu  Ile  Asp  His  Tyr  Val  Gly  Pro  Ala  Gln  Pro  Val  Pro
                100                      105                      110

Gly  Gly  Pro  Pro  Pro  Ser  Arg  Gly  Ser  Val  Pro  Val  Leu  Arg  Ala  Phe
           115                      120                      125

Gly  Val  Thr  Asp  Glu  Gly  Phe  Ser  Val  Cys  Cys  His  Ile  His  Gly  Phe
      130                      135                      140

Ala  Pro  Tyr  Phe  Tyr  Thr  Pro  Ala  Pro  Pro  Gly  Phe  Gly  Pro  Glu  His
145                      150                      155                      160

Met  Gly  Asp  Leu  Gln  Arg  Glu  Leu  Asn  Leu  Ala  Ile  Ser  Arg  Asp  Ser
                165                      170                      175

Arg  Gly  Gly  Arg  Glu  Leu  Thr  Gly  Pro  Ala  Val  Leu  Ala  Val  Glu  Leu
           180                      185                      190

Cys  Ser  Arg  Glu  Ser  Met  Phe  Gly  Tyr  His  Gly  His  Gly  Pro  Ser  Pro
      195                      200                      205

Phe  Leu  Arg  Ile  Thr  Val  Ala  Leu  Pro  Arg  Leu  Val  Ala  Pro  Ala  Arg
      210                      215                      220

Arg  Leu  Leu  Glu  Gln  Gly  Ile  Arg  Val  Ala  Gly  Leu  Gly  Thr  Pro  Ser
225                      230                      235                      240

Phe  Ala  Pro  Tyr  Glu  Ala  Asn  Val  Asp  Phe  Glu  Ile  Arg  Phe  Met  Val
                245                      250                      255

Asp  Thr  Asp  Ile  Val  Gly  Cys  Asn  Trp  Leu  Glu  Leu  Pro  Ala  Gly  Lys
                260                      265                      270

Tyr  Ala  Leu  Arg  Leu  Lys  Glu  Lys  Ala  Thr  Gln  Cys  Gln  Leu  Glu  Ala
           275                      280                      285

Asp  Val  Leu  Trp  Ser  Asp  Val  Val  Ser  His  Pro  Pro  Glu  Gly  Pro  Trp
      290                      295                      300

Gln  Arg  Ile  Ala  Pro  Leu  Arg  Val  Leu  Ser  Phe  Asp  Ile  Glu  Cys  Ala
305                      310                      315                      320

Gly  Arg  Lys  Gly  Ile  Phe  Pro  Glu  Pro  Glu  Arg  Asp  Pro  Val  Ile  Gln
                325                      330                      335
```

-continued

| | | | | | | | | | | | | | | |
|---|---|---|---|---|---|---|---|---|---|---|---|---|---|---|
| Ile | Cys | Ser | Leu 340 | Gly | Leu | Arg | Trp 345 | Gly | Glu | Pro | Glu | Pro 350 | Phe | Leu | Arg |
| Leu | Ala | Leu 355 | Thr | Leu | Arg | Pro | Cys 360 | Ala | Pro | Ile | Leu | Gly 365 | Ala | Lys | Val |
| Gln | Ser | Tyr 370 | Glu | Lys | Glu | Glu | Asp 375 | Leu | Leu | Gln | Ala 380 | Trp | Ser | Thr | Phe |
| Ile 385 | Arg | Ile | Met | Asp | Pro 390 | Asp | Val | Ile | Thr | Gly 395 | Tyr | Asn | Ile | Gln | Asn 400 |
| Phe | Asp | Leu | Pro | Tyr 405 | Leu | Ile | Ser | Arg | Ala 410 | Gln | Thr | Leu | Lys | Val 415 | Gln |
| Thr | Phe | Pro | Phe 420 | Leu | Gly | Arg | Val | Ala 425 | Gly | Leu | Cys | Ser | Asn 430 | Ile | Arg |
| Asp | Ser | Ser 435 | Phe | Gln | Ser | Lys | Gln 440 | Thr | Gly | Arg | Arg | Asp 445 | Thr | Lys | Val |
| Val | Ser | Met 450 | Val | Gly | Arg | Val 455 | Gln | Met | Asp | Met | Leu 460 | Gln | Val | Leu | Leu |
| Arg 465 | Glu | Tyr | Lys | Leu | Arg 470 | Ser | His | Thr | Leu | Asn 475 | Ala | Val | Ser | Phe | His 480 |
| Phe | Leu | Gly | Glu | Gln 485 | Lys | Glu | Asp | Val | Gln 490 | His | Ser | Ile | Ile | Thr 495 | Asp |
| Leu | Gln | Asn | Gly | Asn 500 | Asp | Gln | Thr | Arg | Arg 505 | Arg | Leu | Ala | Val | Tyr 510 | Cys |
| Leu | Lys | Asp 515 | Ala | Tyr | Leu | Pro | Leu 520 | Arg | Leu | Leu | Glu | Arg 525 | Leu | Met | Val |
| Leu | Val | Asn 530 | Ala | Val | Glu | Met 535 | Ala | Arg | Val | Thr | Gly 540 | Val | Pro | Leu | Ser |
| Tyr 545 | Leu | Leu | Ser | Arg | Gly 550 | Gln | Gln | Val | Lys | Val 555 | Val | Ser | Gln | Leu | Leu 560 |
| Arg | Gln | Ala | Met | His 565 | Glu | Gly | Leu | Leu | Met 570 | Pro | Val | Val | Lys | Ser 575 | Glu |
| Gly | Gly | Glu | Asp 580 | Tyr | Thr | Gly | Ala | Thr 585 | Val | Ile | Glu | Pro | Leu 590 | Lys | Gly |
| Tyr | Tyr | Asp 595 | Val | Pro | Ile | Ala | Thr 600 | Leu | Asp | Phe | Ser | Ser 605 | Leu | Tyr | Pro |
| Ser | Ile | Met 610 | Met | Ala | His | Asn 615 | Leu | Cys | Tyr | Thr | Thr 620 | Leu | Leu | Arg | Pro |
| Gly 625 | Thr | Ala | Gln | Lys | Leu 630 | Gly | Leu | Thr | Glu | Asp 635 | Gln | Phe | Ile | Arg | Thr 640 |
| Pro | Thr | Gly | Asp | Glu 645 | Phe | Val | Lys | Thr | Ser 650 | Val | Arg | Lys | Gly | Leu 655 | Leu |
| Pro | Gln | Ile | Leu 660 | Glu | Asn | Leu | Leu | Ser 665 | Ala | Arg | Lys | Arg | Lys 670 | Ala |
| Glu | Leu | Ala | Lys 675 | Glu | Thr | Asp | Pro 680 | Leu | Arg | Arg | Gln | Val 685 | Leu | Asp | Gly |
| Arg | Gln 690 | Leu | Ala | Leu | Lys | Val 695 | Ser | Ala | Asn | Ser | Val 700 | Tyr | Gly | Phe | Thr |
| Gly 705 | Ala | Gln | Val | Gly | Lys 710 | Leu | Pro | Cys | Leu | Glu 715 | Ile | Ser | Gln | Ser | Val 720 |
| Thr | Gly | Phe | Gly | Arg 725 | Gln | Met | Ile | Glu | Lys 730 | Thr | Lys | Gln | Leu | Val 735 | Glu |
| Ser | Lys | Tyr | Thr 740 | Val | Glu | Asn | Gly | Tyr 745 | Ser | Thr | Ser | Ala | Lys 750 | Val | Val |
| Tyr | Gly | Asp 755 | Thr | Asp | Ser | Val | Met 760 | Cys | Arg | Phe | Gly | Val 765 | Ser | Ser | Val |

Ala Glu Ala Met Ala Leu Gly Arg Glu Ala Ala Asp Trp Val Ser Gly
770                     775                 780

His Phe Pro Ser Pro Ile Arg Leu Glu Phe Glu Lys Val Tyr Phe Pro
785             790                 795                         800

Tyr Leu Leu Ile Ser Lys Lys Arg Tyr Ala Gly Leu Leu Phe Ser Ser
                805                 810                 815

Arg Pro Asp Ala His Asp Arg Met Asp Cys Lys Gly Leu Glu Ala Val
            820             825                 830

Arg Arg Asp Asn Cys Pro Leu Val Ala Asn Leu Val Thr Ala Ser Leu
            835             840                 845

Arg Arg Leu Leu Ile Asp Arg Asp Pro Glu Gly Ala Val Ala His Ala
850                 855                 860

Gln Asp Val Ile Ser Asp Leu Leu Cys Asn Arg Ile Asp Ile Ser Gln
865             870                 875                     880

Leu Val Ile Thr Lys Glu Leu Thr Arg Ala Ala Ser Asp Tyr Ala Gly
                885                 890                 895

Lys Gln Ala His Val Glu Leu Ala Glu Arg Met Arg Lys Arg Asp Pro
            900                 905                 910

Gly Ser Ala Pro Ser Leu Gly Asp Arg Val Pro Tyr Val Ile Ile Ser
            915             920                 925

Ala Ala Lys Gly Val Ala Ala Tyr Met Lys Ser Glu Asp Pro Leu Phe
930                 935                 940

Val Leu Glu His Ser Leu Pro Ile Asp Thr Gln Tyr Tyr Leu Glu Gln
945             950                 955                     960

Gln Leu Ala Lys Pro Leu Leu Arg Ile Phe Glu Pro Ile Leu Gly Glu
            965                 970                 975

Gly Arg Ala Glu Ala Val Leu Leu Arg Gly Asp His Thr Arg Cys Lys
            980                 985                 990

Thr Val Leu Thr Gly Lys Val Gly Gly Leu Leu Ala Phe Ala Lys Arg
        995             1000                1005

Arg Asn Cys Cys Ile Gly Cys Arg Thr Val Leu Ser His Gln Gly Ala
    1010            1015                1020

Val Cys Glu Phe Cys Gln Pro Arg Glu Ser Glu Leu Tyr Gln Lys Glu
1025            1030                1035                    1040

Val Ser His Leu Asn Ala Leu Glu Glu Arg Phe Ser Arg Leu Trp Thr
            1045                1050                1055

Gln Cys Gln Arg Cys Gln Gly Ser Leu His Glu Asp Val Ile Cys Thr
        1060                1065                1070

Ser Arg Asp Cys Pro Ile Phe Tyr Met Arg Lys Lys Val Arg Lys Asp
        1075            1080                1085

Leu Glu Asp Gln Glu Gln Leu Leu Arg Arg Phe Gly Pro Pro Gly Pro
    1090                1095                1100

Glu Ala Trp
1105

( 2 ) INFORMATION FOR SEQ ID NO:3:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO -continued (iv) ANTI-SENSE: NO (xi) SEQUENCE DESCRIPTION: SEQ ID NO:3:

Asn Gly Asn Asn Gln Thr Arg Arg Arg Leu Ala Val Tyr Cys Leu Lys
1               5                   10                  15

Asp Ala Tyr Leu Pro Leu Arg Leu
            20

(2) INFORMATION FOR SEQ ID NO:4:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:4:

Asn Gly Asn Asp Gln Thr Arg His Arg Leu Ala Val Tyr Cys Leu Lys
1               5                   10                  15

Asp Ala Tyr Leu Pro Leu Arg Leu
            20

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

CCTGGAACAG GGCATCCG    18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

CGATGACAGT GGCTCCCG    18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

TGTCAGCATG GTGGGCCG 18

( 2 ) INFORMATION FOR SEQ ID NO:8:

( i ) SEQUENCE CHARACTERISTICS:
                ( A ) LENGTH: 24 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:8:

Asn Gly Asn Asp Gln Thr Arg Arg Arg Leu Ala Val Tyr Cys Leu Lys
1               5                   10                  15

Asp Ala Phe Leu Pro Leu Arg Leu
            20

( 2 ) INFORMATION FOR SEQ ID NO:9:

( i ) SEQUENCE CHARACTERISTICS:
                ( A ) LENGTH: 24 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
                ( A ) ORGANISM: Saccharomyces cerevisiae ( x i ) SEQUENCE DESCRIPTION: SEQ ID NO:9:

Asn Gly Asp Ser Glu Thr Arg Arg Arg Leu Ala Val Tyr Cys Leu Lys
1               5                   10                  15

Asp Ala Tyr Leu Pro Leu Arg Leu
            20

( 2 ) INFORMATION FOR SEQ ID NO:10:

( i ) SEQUENCE CHARACTERISTICS:
                ( A ) LENGTH: 24 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal (vi) ORIGINAL SOURCE:
    (A) ORGANISM: Saccharomyces pombe (xi) SEQUENCE DESCRIPTION: SEQ ID NO:10:

```
Asn Gly Thr Ala Asp Ser Arg Arg Arg Leu Ala Ile Tyr Cys Leu Lys
 1               5                   10                      15

Asp Ala Tyr Leu Pro Gln Arg Leu
              20
```